United States Patent
Higashi et al.

(10) Patent No.: US 7,434,586 B2
(45) Date of Patent: Oct. 14, 2008

(54) TOBACCO ODOR DEODORIZING PERFUME COMPOSITION, TOBACCO ODOR DEODORANT, CIGARETTE LOW IN SIDESTREAM SMOKE ODOR, AND TOBACCO PACKAGE

(75) Inventors: Nobukazu Higashi, Yokohama (JP); Fumihiro Omori, Yokohama (JP); Tomoko Monobe, Yokohama (JP); Jun Komiya, Yokohama (JP); Satomi Kunieda, Yokohama (JP); Makoto Emura, Ninomiya-machi (JP); Yoichiro Nishizawa, Yokohama (JP); Takeshi Ishizuka, Tokyo (JP); Takahiro Ariyoshi, Chigasaki (JP)

(73) Assignee: Japan Tobacco Inc., Tokyo (JP)

( * ) Notice: Subject to any disclaimer, the term of this patent is extended or adjusted under 35 U.S.C. 154(b) by 142 days.

(21) Appl. No.: 10/429,734

(22) Filed: May 6, 2003

(65) Prior Publication Data

US 2004/0221858 A1 Nov. 11, 2004

Related U.S. Application Data

(63) Continuation of application No. PCT/JP01/09606, filed on Nov. 1, 2001.

(30) Foreign Application Priority Data

Nov. 6, 2000 (JP) ............................. 2000-338127
Nov. 6, 2000 (JP) ............................. 2000-338129
Nov. 6, 2000 (JP) ............................. 2000-338131

(51) Int. Cl.
*A24B 15/30* (2006.01)
*D21H 27/00* (2006.01)

(52) U.S. Cl. ..................... 131/352; 131/274; 131/275; 131/335; 131/365

(58) Field of Classification Search ................. 131/274, 131/275, 276
See application file for complete search history.

(56) References Cited

U.S. PATENT DOCUMENTS 3,006,347 A * 10/1961 Keaton ....................... 131/277
3,970,701 A    7/1976 Sanderson et al.
4,576,742 A    3/1986 Sprecker et al.
4,663,315 A    5/1987 Hasegawa et al.
4,669,490 A *  6/1987 Naegeli et al. ............... 131/276
5,861,147 A *  1/1999 Dodd et al. .................... 424/65
2003/0192562 A1* 10/2003 Higashi et al. ............... 131/365

FOREIGN PATENT DOCUMENTS

| FR | 1 326 683 | 5/1963 |
| FR | 2 338 240 A | 8/1977 |
| FR | 2 790 923 A1 | 9/2000 |
| GB | 1 591 342 | 6/1981 |
| GB | 2 359 750 A | 9/2001 |
| JP | 49-30427 | 3/1974 |
| JP | 49-118841 | 11/1974 |
| JP | 57-102995 | 6/1982 |
| JP | 62-283944 A | 12/1987 |
| JP | 5-70305 A | 3/1993 |
| JP | 5-146285 A | 6/1993 |
| JP | 5-184649 A | 7/1993 |
| JP | 7-82588 A | 3/1995 |
| JP | 9-103473 A | 4/1997 |
| JP | 10-263064 A | 10/1998 |
| JP | 10-279986 A | 10/1998 |
| WO | WO-95/21606 A1 | 8/1995 |
| WO | WO-96/28497 A1 | 9/1996 |
| WO | WO-99/18940 A1 | 4/1999 |
| WO | WO-00/49120 A1 | 8/2000 |
| WO | WO-01/43784 A2 | 6/2001 |

OTHER PUBLICATIONS

Known-Customary Technologies (Perfume), Part I, Perfume in General, Published Jan. 2, 1999.
Yang, *Journal of Wuxi University of Light Industry*, vol. 19, No. 5, pp. 475-478, Sep. 2000.
P.E. Shaw, *J. Agric. Food Chem.*, vol. 27, No. 2, pp. 246-257 (1979).

* cited by examiner

*Primary Examiner*—Philip C Tucker
*Assistant Examiner*—Michael J Felton
(74) *Attorney, Agent, or Firm*—Birch, Stewart, Kolasch & Birch, LLP

(57) ABSTRACT

A tobacco odor deodorant contains the components of at least two component groups selected from five component of (I) octanal, nonanal and/or decanal, (II) linalool, (III) carvone, (IV) methyl anthranilate and/or N-methyl anthranilate, and (V) sinensal and/or orange peel essential oil sinensal fraction.

25 Claims, No Drawings

TOBACCO ODOR DEODORIZING PERFUME COMPOSITION, TOBACCO ODOR DEODORANT, CIGARETTE LOW IN SIDESTREAM SMOKE ODOR, AND TOBACCO PACKAGE

CROSS-REFERENCE TO RELATED APPLICATIONS

This is a Continuation Application of PCT Application No. PCT/JP01/09606, filed Nov. 1, 2001, which was not published under PCT Article 21(2) in English.

This application is based upon and claims the benefit of priority from the prior Japanese Patent Applications No. 2000-338127, filed Nov. 6, 2000; No. 2000-338129, filed Nov. 6, 2000, and No. 2000-338131, filed Nov. 6, 2000, the entire contents of all of which are incorporated herein by reference.

BACKGROUND OF THE INVENTION

1. Field of the Invention

The present invention relates to a tobacco odor deodorizing composition, a tobacco odor deodorizer, a cigarette low in sidestream smoke odor, and a tobacco package.

2. Description of the Related Art

In general, tobacco odor such as sidestream smoke released from a tobacco smoking article such as a cigarette is not desirable to, particularly, the nonsmoker. Particularly, it is a matter of serious concern to suppress the odor of the sidestream smoke released to the surroundings during the smoking.

One of the measures for suppressing the odor of the tobacco sidestream is to deodorize the tobacco sidestream smoke released during the smoking from the tobacco smoking article to the surroundings, such as within a room. In general, in order to deodorize the malodor released to the surroundings, a method is employed in which a substance producing a very strong aroma is used as a deodorant, whose strong aroma is mixed with the malodor to shield the malodor (see "Known-Customary Technologies (Perfume), Part I, Perfume In General, Published on Jan. 29, 1999").

However, in the conventional deodorant, used is a perfume having an intensity higher than that of the smell, with the result that the intensity of the odor after the mixing of the perfume is considerably higher than that before the mixing, resulting in production of an unpleasant feel in many cases. Also, even if it is possible to shield the smell felt before the mixing with the perfume, the odor after the mixing newly produces in many cases another unpleasant feel. It follows that the conventional deodorant fails to basically improve the unpleasantness of the odor.

Another measure for suppressing the odor of the tobacco sidestream smoke is to add a perfume for masking the odor of the sidestream smoke to the tobacco smoking article so as to prevent the odor of the sidestream smoke from being released from the tobacco smoking article itself. For example, in order to improve the odor of the tobacco sidestream smoke released to the surroundings during the static burn of a cigarette, it is proposed to add a perfume for masking the unpleasant odor to the wrapper paper sheet of the cigarette.

However, it has been found that the conventional perfume for masking the odor of the sidestream smoke, which certainly lowers the odor of the tobacco sidestream smoke, also lowers the tobacco aroma tasted as the tobacco mainstream smoke. It has also been found that the fragrance of the perfume itself is produced relatively strongly, with the result that the intensity of the overall odor generated during the static burn of a cigarette is increased.

Under the circumstances, an object of the present invention is to provide a tobacco odor deodorizing composition and a tobacco odor deodorant, which permits masking the tobacco odor without increasing the overall odor after the mixing with the odor of the sidestream smoke released to the surroundings during the smoking to an unpleasant level and without newly producing another unpleasant odor after the mixing with the odor of the sidestream smoke.

Another object of the present invention is to provide a cigarette which permits preventing the intensity of the overall odor generated during the static burn of the cigarette from being significantly increased and which also permits suppressing the odor of the sidestream smoke.

BRIEF SUMMARY OF THE INVENTION

As a result of extensive research conducted in an effort to achieve the objects described above, the present inventors have found that a mandarin orange essential oil fraction having terpene hydrocarbons substantially removed therefrom is effective for eliminating the tobacco odor, and that a mixture containing at least two components of five component groups selected from the constituting components of the essential oil fraction noted above is capable of masking the tobacco odor without increasing the intensity of the overall odor after the mixing of the fragrance of the mixture with the odor of the sidestream smoke released to the surroundings during the smoking to an unpleasant level and without causing the odor after the mixing of the fragrance with the odor of the sidestream smoke to generate another new unpleasant odor. It has also been found that a mixture containing at least two components of five component groups selected from the constituting components of the mandarin orange essential oil fraction is capable of reducing the sidestream smoke odor generated from the cigarette itself without significantly increasing the intensity of the overall odor that is generated during the static burn of the cigarette.

To be more specific, according to a first aspect of the present invention, there is provided a tobacco odor deodorizing composition, which contains at least two component groups selected from five component groups (I) to (V) given below:

(I) octanal, nonanal and/or decanal;
(II) linalool;
(III) carvone;
(IV) methyl anthranilate and/or N-methyl anthranilate; and
(V) sinensal and/or orange peel essential oil sinensal fraction.

According to a second aspect of the present invention, there is provided a tobacco odor deodorant, comprising a tobacco odor deodorizing composition according to the present invention and a carrier carrying the deodorizing composition.

According to a third aspect of the present invention, there are provided perfumes, cosmetics, foods, external skin remedis, oral compositions, or sanitary materials, which contain 0.0005 to 20 mass % of the tobacco odor deodorant of the present invention.

According to a fourth aspect of the present invention, there is provided a cigarette comprising a tobacco rod including a tobacco filler material and a cigarette wrapper paper sheet wrapping the outer circumferential surface of the tobacco filler material, the cigarette carrying a sidestream smoke odor reducing agent containing at least two component groups selected from five component groups (I) to (V) given below:

(I) octanal, nonanal and/or decanal;
(II) linalool;
(III) carvone;
(IV) methyl anthranilate and/or N-methyl anthranilate; and
(V) sinensal and/or orange peel essential oil sinensal fraction.

Further, according to a fifth aspect of the present invention, there is provided a tobacco package housing tobacco rods each including a tobacco filler material and a cigarette wrapper paper sheet wrapping the outer circumferential surface of the tobacco filler material, the tobacco package containing a sidestream smoke odor reducing agent of the present invention.

DETAILED DESCRIPTION OF THE INVENTION

The present invention will now be described in detail.

The tobacco odor deodorizing composition of the present invention contains at least two groups of components selected from five component groups (I) to (V) given below:
(I) octanal, nonanal and/or decanal;
(II) linalool;
(III) carvone;
(IV) methyl anthranilate and/or N-methyl anthranilate; and
(V) sinensal and/or orange peel essential oil sinensal fraction.

Among the components noted above, linalool may be any of a d-form, an l-form and a racemic form, carvone may be any of an l-form, a d-form and a racemic form, and sinensal may be any of an α-form, a β-form and a mixture thereof. The orange peel essential oil sinensal fraction represents α,β-sinensal (characteristic component), which can be obtained by fractionation of an essential oil (generally called cold pressed oil) collected when cold or at room temperature, or a fraction rich in the α,β-sinensal component. For example, it is possible to use "sinensal 20/10A National" (trade name) available from R.C. Treat Inc. The components constituting the component groups (I) to (V) are called specified components hereinafter in some cases.

The tobacco odor deodorizing perfume composition of the present invention comprises two specified component system to five specified component system given below under the conditions that, where at least two of components (a) to (c) of component group (I) are contained in the form of a mixture, the mixture is regarded as a single component, that, where components (a) and (b) of component group (IV) are contained in the form of a mixture, the mixture is regarded as a single component, and that, where components (a) and (b) of component group (V) are contained in the form of a mixture, the mixture is regarded as a single component. This is also the case with the present invention.

<Two Specified Component System>
A combination of (I)(a), (I)(b) and/or (I)(c) with (II), (III), (IV)(a) and/or (IV)(b) or (V)(a) and/or (V)(b);
A combination of (II) with (III), (IV)(a) and/or (IV)(b) or (V)(a) and/or (V)(b);
A combination of (III) with (IV)(a) and/or (IV)(b) or (V)(a) and/or (V)(b); or
A combination of (IV)(a) and/or (IV)(b) with (V)(a) and/or (V)(b).

In the two specified component system, it is particularly desirable to employ the combination of (I)(a), (I)(b) and/or (I)(c) with (II), the combination of (I)(a), (I)(b) and/or (I)(c) with (III), the combination of (I)(a), (I)(b) and/or (I)(c) with (IV)(a) and/or (IV)(b), the combination of (I)(a), (I)(b) and/or (I)(c) with (V)(a) and/or (V)(b), the combination of (II) with (IV)(a) and/or (IV)(b), the combination of (II) and (V)(a) and/or (V)(b), the combination of (III) with (IV)(a) and/or (IV)(b), the combination of (III) with (V)(a) and/or (V)(b), and the combination of (IV) with (V)(a) and/or (V)(b).

<Three Specified Component System>
A combination of (I)(a), (I)(b) and/or (I)(c) with (II) and with (III), (IV)(a) and/or (IV)(b) or (V)(a) and/or (V)(b);
A combination of (I)(a), (I)(b) and/or (I)(c) with (III) and with (IV)(a) and/or (IV)(b) or (V)(a) and/or (V)(b);
A combination of (II) with (III) and with (IV)(a) and/or (IV)(b) or (V)(a) and/or (V)(b); or
A combination of (I)(a), (I)(b) and/or (I)(c), (II) and/or (III) with (IV)(a) and/or (IV)(b) and with (V)(a) and/or (V)(b).

<Four Specified Component System>
A combination of (I)(a), (I)(b) and/or (I)(c) with (II) and with (III) and with (IV)(a) and/or (IV)(b) or (V)(a) and/or (V)(b);
A combination of (II) with (III) and with (IV)(a) and/or (IV)(b), and with (V)(a) and/or (V)(b); or
A combination of (I)(a), (I)(b) and/or (I)(c) with (II) and/or (III) and with (IV)(a) and/or (IV)(b), and with (V)(a) and/or (V)(b).

(Five Specified Component System)
A combination of (I)(a), (I)(b) and/or (I)(c) with (II) and with (III), and with (IV)(a) and/or (IV)(b), and with (V)(a) and/or (V)(b).

However, in a preferred embodiment of the present invention, the deodorizing composition of the present invention comprises at least two components, preferably at least three components, selected from the group consisting of octanal, linalool, carvone, methyl anthranilate and an orange peel essential oil sinensal fraction.

The desired effect produced by the deodorizing composition of the present invention is rendered more prominent with increase in the number of specified components. To be more specific, the three specified component system is more desirable than the two specified component system, and the four specified component system is more desirable than the three specified component system. The five specified component system provides the most desirable deodorizing composition of the present invention.

In the deodorizing composition of the present invention, the five specified components are mixed desirably at a weight ratio of (I):(II):(III):(IV):(V)=2-6:3-10:0.5-2.5:0.5-20:0.1-3. It should be noted that the weight ratio given above is applied as it is in respect of the weight ratio of the two specified components in the two specified component system, in respect of the weight ratio of the three specified components in the three specified component system, and in respect of the weight ratio of the four specified components in the four specified component system. This is also the case with the ratio of the specified components. Namely, if the weight ratio of (I):(II):(III):(IV):(V) given above is represented by A:B:C:D:E for the sake of brevity, the ratio of, for example, (II) to (III) in the two component system of (II) and (III) should desirably be B:C, and the ratio of (I) to (IV) in the two component system of (I) and (IV) should desirably be A:D. Likewise, the ratio of (I):(II):(III) in the three component system of (I), (II) and (III) should desirably be A:B:C, and the ratio of (II): (IV):(V) in the three component system of (II), (IV) and (V) should desirably be B:D:E. Also, the ratio of, for example, (I):(II):(III):(IV) in the four component system of (I), (II), (III) and (IV) should desirably be A:B:C:D, and the ratio of (II): (III):(IV):(V) in the four component system of (II), (III), (IV) and (V) should desirably be B:C: D:E.

In the deodorizing composition of the present invention, it is particularly desirable for the components of the composition to be mixed at a weight ratio that permits substantially maintaining the ratio of presence of the specified components in a mandarin orange essential oil. Incidentally, of the specified components, the orange peel essential oil sinensal fraction (V)(b) is not contained as it is in the mandarin orange essential oil. However, since the component (V)(b) is equivalent to the component (V)(a) sinensal, the ratio of presence of component (V) is equal to the ratio of presence of sinensal in the mandarin orange essential oil. In other words, the particularly desirable weight ratio of the specified components (I): (II):(III):(IV):(V) in the deodorizing composition of the present invention is 3-5:7-10:1.0-2.0:1.0-3.0:0.5-1.5.

It is possible for the deodorizing composition of the present invention to contain components other than the specified components described above. The other components, which are used preferably in the deodorizing composition of the present invention, include, for example, the mandarin orange essential oil components other than the specified components described above. To be more specific, the other mandarin orange essential oil components, which can be contained in the deodorizing composition of the present invention, include, for example, alcohol components such as 4-terpineol, α-terpineol, octanol, thymol, heptanol, cis-carveol, perilaalcohol, p-menthane 1,8-diol; aldehyde components such as geranial, citronellal and dodecanal; and limonene oxide. The deodorizing composition of the present invention preferably contains the specified components in total in an amount of at least 0.1 mass %, preferably at least 5 mass %, and most preferably at least 30 mass %.

It is possible to house the tobacco odor deodorizing composition of the present invention in a suitable container and to dispose the container as a tobacco deodorant within a room.

However, it is possible for the tobacco odor deodorizing composition of the present invention to be carried by a suitable carrier so as to provide a tobacco odor deodorant.

In this case, it is possible to add further perfume components generally used as a component producing a deodorizing effect to the tobacco odor deodorizing composition of the present invention. The deodorizing perfumes used in the present invention include, for example, various synthetic perfumes, natural perfumes, synthetic essential oils, natural essential oils and a citrus oil. To be more specific, it is possible to use a wide range of deodorizing perfumes described in, for example, "Known Customary Technologies (Perfume), Part I, Perfumes in general, 2•6•16 Masking Agent pp 230-250 (1999)".

The forms of the tobacco odor deodorant of the present invention includes a liquid, a solid, a powder, a gel, a mist, or an aerosol.

On the other hand, the carrier may be a liquid base material, a solid base material, a powdery base material, a gel base material, a mist base material or an aerosol base material as the carrier in accordance with the selected form of deodorant.

In the present invention, the methods whereby the deodorizing composition is carried by the carrier include, in the case of a liquid base material, a gel base material or a mist base material, using, for example, a surfactant, a gelling agent or a water-soluble high molecular weight material as the carrier, and allowing the deodorizing composition to be carried within the micell or gel formed by the carrier. On the other hand, in the case of a solid base material, a powdery base material or an aerosol base material, the deodorizing composition may be carried on the surface of the powdery or granular formed material such as silica gel.

The liquid base material used in the present invention includes, for example, nonionic surfactants such as polyoxyethylene sorbitan mono-oleate, polyoxyethylene sorbitan monostearate, and polyoxyethylene cured castor oil; and anionic surfactants such as polyoxy lauryl ether sodium phosphate.

The gel base materials include those formed from, for example, gel materials extracted from various plants, animals, algae, and microorganisms such as carrageenan, juran gum, tragacanth, agar-agar, gelatin, and pectin; metal soaps used as gel materials such as sodium stearate and sodium 12-hydroxystearate; and water-soluble organic high molecular weight materials such as polyvinyl alcohol, a cellulose derivative, and a starch derivative.

The solid base materials include, for example, powdery or granular formed materials such as silica gel, alumina, zeolite, diatomaceous earth, calcium silicate, pulp, and cellulose.

The mist base materials include, for example, nonionic surfactants such as polyoxyethylene sorbitan monooleate, polyoxyethylene sorbitan monostearate, and polyoxyethylene cured castor oil; and anionic surfactants such as sodium polyoxylauryletherphosphate.

Further, the aerosol base materials used in the present invention include, for example, spherical formed materials such as a spherical silica gel.

In the present invention, the amount of the tobacco odor deodorant such as the liquid deodorant, the solid deodorant, the powdery deodorant, the gel deodorant, the mist deodorant or the aerosol deodorant is controlled optionally in accordance with the expected effect and function of the deodorant. However, it is generally desirable for the deodorant to contain about 0.005 to 50 mass % of the tobacco odor deodorizing composition.

In putting the tobacco odor deodorant of the present invention to practical use, it is possible to add the deodorant to the perfumes and cosmetics, the foods, the external remedies, the compositions for the oral cavity, or the sanitary materials.

The perfumes and cosmetics include, for example, an emollient lotion, an astringent lotion, a wiping lotion, a milk lotion, a body lotion, an after-shave lotion, a massage cream, a cleansing cream or gel, an antiperspirant, an eye pack agent, shampoos, hair creams, hair tonics, pomades, rinses, conditioners, hair-growing lotions and other cosmetic base materials for the hair; toilet powders, a lipstick, and other cosmetic base materials and detergents for cosmetics.

The foods include, for example, drinking beverage such as a fruit juice beverage, fruit liquors, a milk, a carbonic beverage, and drinks; cold confectionery such as ice creams, sherbets, and ice candies; favorite foods and drinks such as Japanese and Western confectionery, jams, candies, jellies, gums, breads, coffees, cocoas, black teas, oolong teas, and green teas; soups such as Japanese style soup, Western style soup, and Chinese style soup; flavors, seasonings, various precooked drinks and foods, and various snack foods.

The external remedies include, for example, an aerosol preparation, a cataplasm agent, an ointment, and a bathing agent.

The oral compositions includes, for example, a dentifrice, an oral detergent, a mouth wash, and a chewing gum.

Further, the sanitary materials include, for example, washing detergents, detergent for disinfection, detergents for odor prevention, indoor fragrance producing agents, indoor deodorants, soaps, detergents for washing dishes, softeners, furniture cares, and other sanitary detergents; various sanitary materials such as tissue paper, and toilet paper; and sanitary medicines such as a flavor imparting agent for facilitating the dosage of a medicine.

It suffices for the tobacco odor deodorant of the present invention to contain as indispensable ingredients the 2 or more, preferably 3 or more specified components noted above, and a carrier carrying these components. Where the deodorant of the present invention is applied to perfumes, cosmetics, foods, external remedies, oral compositions, or sanitary materials, it is possible to apply the deodorant directly or in the form of a solution having the deodorant dissolved in, for example, alcohols, or polyhydric alcohols such as propylene glycol, or glycerin; in the form of an emulsion emulsified by using an emulsifying agent such as natural rubbery materials including gum arabic and tragacanth, glycerin fatty acid ester, or a sucrose fatty acid ester; in the form of a powder prepared by using an excipient such as natural gum substance including gum arabic, gelatin, or dextrin; in the form of a soluble or dispersible material that is made soluble or dispersible by using a surfactant such as a nonionic surfactant, an anionic surfactant, a cationic surfactant or an amphoteric surfactant; or in the form of a microcapsule prepared by the processing with an encapsulizing agent. The form of the deodorant can be selected appropriately in accordance with the object of applying the deodorant.

Further, it is possible to have the tobacco odor deodorant of the present invention included in an inclusion agent such as cyclodextrin so as to stabilize and to release gradually the deodorant. These are selected for use appropriately in a manner to be adapted for the form of the final product of the deodorant such as a liquid form, a solid form, a powdery form, a gel form, a mist form or an aerosol form.

Also, the tobacco odor deodorant of the present invention is used in some cases in combination with other deodorants such as a perfume, an oxidizing agent, a reducing agent, a neutralizing agent, an inorganic deodorant such as an inorganic base, an inorganic acid, a metal oxide, a chlorine compound, ozone, and a porous material, and surfactants such as a nonionic surfactant, an anionic surfactant, a cationic surfactant and amphoteric surfactant.

Incidentally, the addition amount of the tobacco odor deodorant to the final products such as the perfumes and cosmetics, the foods, the external remedies, the oral composition, and the sanitary material can be determined optionally in accordance with the expected effect and function, though about 0.0005 to 20 mass % of the tobacco odor deodorant is added in general based on the total mass of the final product.

Further, the tobacco odor deodorizing composition of the present invention can provide a tobacco sidestream smoke odor reducing agent for reducing the tobacco sidestream smoke odor generated from the cigarette itself.

The sidestream smoke odor reducing agent of the present invention is carried by a cigarette. The cigarette comprises a tobacco rod including a tobacco filler material and a cigarette wrapper paper sheet wrapping the outer circumferential surface of the tobacco filler material. The tobacco filler material includes tobacco shreds. The tobacco shreds may be expanded. It is possible to employ a known expanding method for expanding the tobacco shreds. Also, it is possible to use any wrapper paper sheet suitable for wrapping the outer circumferential surface of the tobacco filler material so as to provide a cigarette. Incidentally, the cigarette of the present invention may be provided with a filter plug at one end of the tobacco rod.

The sidestream smoke odor reducing agent of the present invention can be carried by the cigarette in various forms. For example, the sidestream smoke odor reducing agent of the present invention can be carried by the cigarette by adding the odor reducing agent to the tobacco filler material, by coating the cigarette wrapper paper sheet with the odor reducing agent, or by adding the odor reducing agent to a seam paste for bonding the cigarette wrapper paper sheet. The effect of reducing the sidestream smoke odor is not particularly dependent on the application positions such as the tobacco shreds. However, it is possible to add the sidestream smoke odor reducing agent of the present invention to the tobacco filler material by the ordinary technology of imparting flavor to the tobacco shreds. Naturally, the particular addition method is convenient. In any case, it is desirable for the sidestream smoke odor reducing agent of the present invention to be applied uniformly. Incidentally, where the cigarette of the present invention has a filter plug at one end of the tobacco rod, the filter plug is connected in general to the tobacco rod by using a so-called tip paper. It is possible to coat the tip paper or a filter wrapper paper sheet with the sidestream smoke odor reducing agent of the present invention.

The sidestream smoke odor reducing agent of the present invention is carried by the cigarette of the present invention such that the total amount of the specified components amount to preferably at least 0.01 mg per cigarette, more preferably, 0.02 mg to 0.2 mg per cigarette.

Further, the sidestream smoke odor reducing agent of the present invention can be housed in a tobacco package. The tobacco package contains a plurality of cigarettes, e.g., 20 cigarettes, each comprising a tobacco rod including a tobacco filler material and a cigarette wrapper paper sheet wrapping the outer circumferential surface of the tobacco filler material as well as the sidestream smoke odor reducing agent of the present invention. The sidestream smoke odor reducing agent of the present invention can be housed in the tobacco package by, for example, applying it to an aluminum foil. The sidestream smoke odor reducing agent of the present invention housed in the tobacco package is migrated into the cigarette before the tobacco package is opened so as to decrease the sidestream smoke odor in the smoking time.

The present invention will now be described by way of its Examples, which do not limit the present invention, and the present invention is not limited to these Examples.

The organoleptic evaluation methods (odor bag method and room method) employed in the following Examples are as follows:

A. Odor Bag Method (Deodorizing Composition):

Prepared are a parallelepiped chamber (sidestream smoke chamber) having an inner volume of 405 L and equipped, at an upper portion of the inside wall, with an air bag mounting tube communicating with the outer atmosphere, and at a lower portion of the inside wall, with a through-hole for insertion of an inner air suction port, and also having a cigarette mounting tool at the inside wall, as well as an air collecting box available on the market. The air collecting box, which has an inner volume slightly larger than 10 L, has an inner air suction port formed in a lower portion of the inside wall and a discharge hole formed in a lower portion of the inside wall facing the inside wall having the air suction port formed therein.

An air bag having an inner volume of 10 L is mounted to the air bag mounting tube of the sidestream smoke chamber, and a collecting bag having an inner volume of 10 L is mounted to the suction port of the air collecting box. Then, the suction port of the air collecting box is inserted into the through-hole of the sidestream smoke chamber. Further, the discharge port of the air collecting box is connected to the air bag mounting tube of the sidestream smoke chamber by using a hose with a vacuum pump interposed therebetween such that it is possible to suck the air inside the air collecting box and to discharge the sucked air into the air bag mounted inside the chamber, establishing a closed system.

Under the condition described above, a cigarette is mounted to the cigarette mounting tool inside the chamber and is subjected to the static burn so as to generate a sidestream smoke.

After the static burn of the cigarette is completed, the vacuum pump is driven so as to establish a negative pressure inside the air collecting box and at the same time to increase the pressure inside the sidestream smoke chamber by the air discharge into the air bag, thereby allowing the air containing the sidestream smoke within the sidestream smoke chamber to be collected in the collecting bag within the collecting box.

The collecting box is detached from the sidestream smoke chamber under the state that the collecting bag collecting the air containing the sidestream smoke is left housed in the collecting box. Then, the collecting box is connected to a diluting line. The diluting line comprises a line for supplying, by using a pump, a deodorized air into an odor bag having an inner volume of 3 L and connected to its downstream terminal and a branched line branched from the line for supplying the deodorized air so as to be connected to the suction port of the collecting box. Each of these lines is provided with a flow rate control valve. The collecting box is pressurized by a pressurizing pump so as to permit the air within the collecting bag to be supplied into the odor bag through the branched line.

The composition to be evaluated is injected by a syringe into the odor bag thus prepared (diluted to have a concentration equal to that in the case of combusting a single cigarette per 17 m$^3$) and evaporated. The odor bag having the perfume composition injected therein is presented in blind to the panelist together with an odor bag not having a perfume injected therein for the evaluation by a paired comparison test (method of compulsory selection between the two). The result of the evaluation is reported by the panelist in terms of the items given below:

1. Which bag has a stronger intensity of the overall odor?
2. Which bag has a good odor?
3. Which bag has a stronger tobacco odor?

In each of the evaluation items 1 to 3 given above, the number of panelists selecting the odor bag having the perfume composition injected therein was divided by the number of the entire panelists so as to obtain the result of the evaluation. It follows that the smaller number represents the better result in respect of each of the intensity of the overall odor and the intensity of the tobacco odor. On the other hand, the larger number represents the better result in respect of the quality of the odor. Incidentally, optionally extracted adults who had not received an expert training on the tobacco odor were selected as the panelists B. Odor Bag Method (Cigarette):

The odor of the sidestream smoke of the cigarette was collected and diluted as in the odor bag method (deodorizing composition) described above. An odor bag in respect of a cigarette for a reference case and another odor bag in respect of a cigarette to be evaluated were presented in blind to five expert panelists for the functional evaluation in five stages ranging between point 0 (no odor) and point 4 (highest point).

C. Room Method

Prepared are two rooms (room A and room B) each having a floor area of 31 m$^2$ and a volume of 85 m$^3$, and each being closed except for a door, through which the evaluators enter or leave the room. With the door closed, five reference cigarettes are subjected to static burn within room A. On the other hand, five cigarettes to be evaluated are subjected to static burn within room B, also with the door closed. The panelists are classified into two groups. All the panelists of one group simultaneously enter room A and, after coming out of room A, enter room B. Then, the panelists coming out of room B report the results in respect of the items given below. On the other hand, all the panelists of the other group simultaneously enter room B and, after coming out of room B, enter room A. Then, the panelists coming out of room A report the results in respect of the items given below:

1. In which room did the panelists feel a higher intensity of the overall odor?
2. In which room did the panelists feel an improvement in the odor?
3. In which room did the panelists feel a higher intensity of the tobacco odor?

To obtain the results, the number of panelists who answered, "room B", in which the cigarettes for evaluation were subjected to the static burn, was divided by the number of all the panelists in respect of each of the evaluation items 1 to 3 given above. It follows that a smaller number represents a better result for both the intensity of the overall odor and the intensity of the tobacco odor. On the other hand, a larger number represents a better result in respect of the improvement of the odor. Incidentally, the panelists were randomized adults, who had not received training on the tobacco odor.

PREPARATION EXAMPLES 1 to 18

Tobacco odor deodorizing compositions of the present invention were prepared by mixing the components shown in Tables 1 to 3 given below at the mixing ratios shown in these Tables.

TABLE 1

| | Component mixing ratio (mass %) Preparation Examples | | | | | | |
|---|---|---|---|---|---|---|---|
| Component | 1 | 2 | 3 | 4 | 5 | 6 | 7 |
| OCT | 29 | 69 | 73 | 81 | | | |
| LIN | 71 | | | | 85 | 87 | 92 |
| CAR | | 31 | 27 | | 15 | | |
| MAN | | | | | | 13 | |
| SIN | | | | 19 | | | 8 |
| Amount added* (mg) | 0.112 | 0.046 | 0.047 | 0.041 | 0.096 | 0.097 | 0.091 |

<Explanation of symbols in the Table>
OCT: n-octanal;
LIN: linalool;
CAR: 1-carvone;
MAN: methyl anthranilate;
SIN: sinensal;
Note
*Amount added to odor bag

TABLE 2

| Component | Component mixing ratio (mass %) Preparation Examples | | | | | |
|---|---|---|---|---|---|---|
| | 8 | 9 | 10 | 11 | 12 | 13 |
| OCT | | | 63 | | 49 | 22 |
| LIN | | | | | | 55 |
| CAR | 56 | 67 | 23 | 43 | 22 | 10 |
| MAN | 44 | | | 35 | 18 | 8 |
| SIN | | 33 | 14 | 22 | 11 | 5 |
| Amount added* (mg) | 0.031 | 0.025 | 0.026 | 0.041 | 0.072 | 0.153 |

<Explanation of symbols in the Table>
OCT: n-octanal
LIN: linalool
CAR: l-carvone
MAN: methyl anthranilate
SIN: sinensal
Note
*Amount added to odor bag

TABLE 3

| Component | Component mixing ratio (mass %) Preparation Examples | | | | |
|---|---|---|---|---|---|
| | 14 | 15 | 16 | 17 | 18 |
| OCT | 23.0 | 18.3 | 23 | 18.3 | 22.4 |
| LIN | 21.5 | 17.2 | 21.5 | 17.2 | 54.5 |
| CAR | | | | | 10 |
| MAN | 0.1 | 0.1 | 0.1 | 0.06 | 7.4 |
| N-MAN | 39.0 | 31.3 | 39 | 31.3 | |
| SIN | 12.9 | 10.4 | | | |
| 4-TER | | 2.0 | | 2 | |
| α-TER | | 7.1 | | 7.1 | |
| NON | | 2.3 | | 2.3 | |
| GER | | 5.0 | | 5 | |
| LMO | 3.5 | 6.3 | 3.5 | 6.3 | |
| OEO | | | 12.9 | 10.44 | 5.7 |
| Amount added* (mg) | 0.350 | 0.800 | 0.400 | 0.800 | 0.153 |

<Explanation of symbols in the Table>
OCT: n-octanal; LIN: linalool;
CAR: l-carvone; MAN: methyl anthranilate;
N-MAN: methyl N-methyl anthranilate;
SIN: sinensal; 4-TER: 4-terpineol;
α-TER: α-terpineol; NON: nonanal;
GER: geranial; LMO: cis-limonene oxide;
OEO: orange peel essential oil sinensal fraction
Note
*Amount added to odor bag A tobacco odor deodorizing effect was evaluated by the odor bag method (deodorizing composition) described above in respect of the deodorizing compositions prepared in Preparation Examples 1 to 18. Table 4 shows the result of the evaluation.

TABLE 4

| Tobacco Odor Deodorizing Composition | Results of Evaluation | | | |
|---|---|---|---|---|
| | Intensity of Overall Odor | Improvement of Odor | Intensity of Tobacco Odor | Number of Panelists |
| Preparation Ex. 1 | 0.55 | 0.62 | 0.40 | 31 |
| Preparation Ex. 2 | 0.50 | 0.56 | 0.44 | 31 |
| Preparation Ex. 3 | 0.48 | 0.53 | 0.46 | 32 |
| Preparation Ex. 4 | 0.51 | 0.61 | 0.45 | 32 |
| Preparation Ex. 5 | 0.50 | 0.62 | 0.33 | 31 |
| Preparation Ex. 6 | 0.48 | 0.59 | 0.35 | 33 |
| Preparation Ex. 7 | 0.51 | 0.67 | 0.24 | 31 |
| Preparation Ex. 8 | 0.43 | 0.53 | 0.49 | 33 |
| Preparation Ex. 9 | 0.46 | 0.61 | 0.38 | 32 |
| Preparation Ex. 10 | 0.44 | 0.58 | 0.39 | 33 |
| Preparation Ex. 11 | 0.50 | 0.64 | 0.29 | 28 |
| Preparation Ex. 12 | 0.47 | 0.73 | 0.30 | 30 |
| Preparation Ex. 13 | 0.56 | 0.80 | 0.20 | 25 |
| Preparation Ex. 14 | 0.50 | 0.70 | 0.23 | 30 |
| Preparation Ex. 15 | 0.45 | 0.77 | 0.16 | 31 |
| Preparation Ex. 16 | 0.45 | 0.72 | 0.20 | 29 |
| Preparation Ex. 17 | 0.50 | 0.71 | 0.25 | 28 |
| Preparation Ex. 18 | 0.47 | 0.80 | 0.20 | 30 |

As apparent from Table 4, the deodorizing composition of the present invention, even if mixed with a tobacco odor, permits effectively deodorizing the tobacco odor without significantly increasing the intensity of the entire odor.

Example 1

Granular Deodorant (I) A deodorizing composition for a granular deodorant of the composition shown in Table 5 was prepared by using the deodorizing composition prepared in Preparation Example 13.

TABLE 5

<Deodorizing Composition for Granular Deodorant>

| Components | Amount (parts by mass) |
|---|---|
| 2-methylundecanal | 30 |
| Benzyl acetate | 200 |
| Eucalyptus oil | 50 |
| Hexyl salicylate | 40 |
| Isobornyl acetate | 400 |
| Linalool | 30 |
| Linalyl acetate | 50 |
| Tobacco odor deodorizing composition of Preparation Ex. 13 | 50 |
| Oakmoss absolute | 30 |
| Isocamphylcyclohexanol | 20 |
| Acetylcedrene | 100 |
| Total | 1000 |

(II) Propylene glycol (B) shown in Table 6 below was added to silica gel (C) shown in Table 5 and slowly stirred. After propylene glycol was absorbed by silica gel and the surface of silica gel was dried, the deodorizing composition (A) shown in Table 6 was added to the silica gel and allowed to be absorbed by the silica gel while slowly stirring the silica gel, thereby obtaining a granular deodorant.

TABLE 6

<Granular deodorant>

| Components | Amount (parts by mass) |
| --- | --- |
| (A) Deodorizing composition of Ex. 1 (I) | 10 |
| (B) Propylene glycol | 10 |
| (C) Silica gel B-type | 80 |
| Total | 100 |

Example 2

Granular Deodorant

Propylene glycol (B) shown in Table 7 below was added to silica gel (C) shown in Table 7 and slowly stirred. After propylene glycol was absorbed by silica gel and the surface of silica gel was dried, the deodorizing composition (A) shown in Table 7 was added to the silica gel and allowed to be absorbed by the silica gel while slowly stirring the silica gel, thereby obtaining a granular deodorant.

TABLE 7

<Granular deodorant>

| Components | Amount (parts by mass) |
| --- | --- |
| (A) Tobacco odor deodorizing composition of Preparation Ex. 13 | 10 |
| (B) Propylene glycol | 10 |
| (C) Silica gel B-type | 80 |
| Total | 100 |

Example 3

Mist Deodorant (I) A deodorizing composition for a mist deodorant, having the composition shown in Table 8 below was prepared by using the deodorizing composition prepared in Preparation Example 18.

TABLE 8

<Deodorizing composition for mist deodorant>

| Components | Amount (parts by mass) |
| --- | --- |
| 1-octen-3-ol | 5 |
| Cineol | 50 |
| Coumarin | 20 |
| Geraniol | 50 |
| Lavandine oil | 250 |
| Revosandol (trade name; manufactured by Takasago Koryo Kogyo K.K.)[1] | 10 |
| Linalool | 150 |
| Linalyl acetate | 100 |
| Tobacco odor deodorizing composition of Preparation Ex. 18 | 70 |
| Ethylene brassylate | 50 |
| Orange oil | 75 |
| Terpineol | 50 |
| Terpinyl acetate | 120 |
| Total | 1000 |

Note:
[1] (e)-(R)-2-ethyl-4-(2,2,3-trimethyl-3-cyclopenten-1-yl)-2-buten-1-ol (II) Four components (A) shown in Table 9 below were mixed and dissolved completely. Then, the resultant solution was added to a purified water having methyl paraben, which is one of the components (B) shown in Table 9, dissolved therein in advance, and the mixture was stirred to dissolve the components, thereby obtaining a mist deodorant.

TABLE 9

<Mist deodorant>

| Components | Amount (parts by mass) |
| --- | --- |
| (A) Deodorizing composition of Ex. 3 (I | 0.5 |
| Polyoxyethylene cured castor oil (EO 40) | 1.0 |
| Polyoxyethylene cured castor oil (EO 60) | 0.5 |
| 95% geraniol denatured alcohol | 2.5 |
| (B) Methylparaben | 0.1 |
| Purified water | 95.4 |
| Total | 100 |

Example 4

Mist Deodorant

Four components (A) shown in Table 10 below were mixed and dissolved completely. Then, the resultant solution was added to a purified water having methyl paraben, which is one of the components (B) shown in Table 10, dissolved therein in advance, and the mixture was stirred to dissolve the components, thereby obtaining a mist deodorant.

TABLE 10

<Mist deodorant>

| Components | Amount (parts by mass) |
| --- | --- |
| (A) Tobacco odro deodorant composition of Preparation Ex. 18 | 0.5 |
| Polyoxyethylene cured castor oil (EO 40) | 1.0 |
| Polyoxyethylene cured castor oil (EO 60) | 0.5 |
| 95% geraniol denatured alcohol | 2.5 |
| (B) Methylparaben | 0.1 |
| Purified water | 95.4 |
| Total | 100 |

Example 5

Water-based Deodorant (I) A deodorizing composition for a water-based deodorant having the composition shown in Table 11 below was prepared by using the deodorizing composition prepared in Preparation Example 13.

TABLE 11

<Deodorizing composition for water-based deodorant>

| Components | Amount (parts by mass) |
| --- | --- |
| Nonyl aldehyde | 1 |
| Citronellol | 380 |
| β-damascon | 3 |
| Eugenol | 20 |
| Cis-3-hexen-1-ol | 8 |
| β-ionone | 50 |
| Isocyclocitral | 5 |
| Tobacco odor deodorizing composition of Preparation Ex. 13 | 25 |
| Phenylethyl acetate | 120 |
| Phenylethyl alcohol | 205 |
| Rose oxide | 1 |
| Teaspyran | 2 |
| o-tert-butylcyclohexyl acetate | 180 |
| Total | 1000 |

(II) Purified water, propylene glycol and calcium chloride shown in Table 12 below was stirred until uniform. Then, carrageenan, locust bean gum and methyl paraben were added in small proportions while stirring the mixture, followed by heating the mixture to 80° C. while stirring the mixture. When the mixture was converted into a suspension, the heating was stopped so as to cool the suspension. After cooled to about 65° C., the deodorizing composition for the water-based deodorant of Example 5 (I) and polyoxyethylenesorbitan monooleate were added and stirred. Then, the mixture was kept stirred at 55° C. until the mixture formed a suspension, thereby obtaining a water-based gel deodorant having the composition shown in Table 12 below.

TABLE 12

<Water-based gel deodorant>

| Components | Amount (parts by mass) |
| --- | --- |
| Carrageenan | 2.0 |
| Locust bean gum | 0.4 |
| Methylparaben | 0.1 |
| Purified water | 88.6 |
| Calcium chloride | 0.4 |
| Propylene glycol | 3.0 |
| Deodorizing composition of Ex. 5 (I) | 5.0 |
| Polyoxyethylenesorbitan monooleate | 0.5 |
| Total | 100.0 |

Example 6

Water-based Gel Deodorizing Agent

Purified water, propylene glycol and calcium chloride shown in Table 13 below was stirred until uniform. Then, carrageenan, locust bean gum, and methylparaben were added in small proportions while stirring the mixture, followed by heating the mixture to 80° C. while stirring the mixture. When the mixture was converted into a suspension, the heating was stopped so as to cool the suspension. After cooled to about 65° C., the deodorizing composition prepared in Preparation Example 13 and polyoxyethylenesorbitan monooleate were added and stirred. Then, the mixture was kept stirred at 55° C. until the mixture formed a suspension, thereby obtaining a water-based gel deodorant having the composition shown in Table 13 below.

TABLE 13

<Water-based gel deodorant>

| Components | Amount (parts by mass) |
| --- | --- |
| Carrageenan | 2.0 |
| Locust bean gum | 0.4 |
| Methylparaben | 0.1 |
| Purified water | 88.6 |
| Calcium chloride | 0.4 |
| Propylene glycol | 3.0 |
| Tobacco odor deodorizing composition of Preparation Ex. 13 | 5.0 |
| Polyoxyethylenesorbitan monooleate | 0.5 |
| Total | 100.0 |

Example 7

Oily Gel Deodorant (I) A deodorizing composition for an oily gel deodorant having the composition as shown in Table 14 below was prepared by using the deodorizing composition prepared in Preparation Example 13.

TABLE 14

<Deodorizing composition for oily gel deodorant>

| Components | Amounts (parts by mass) |
| --- | --- |
| Benzyl acetate | 400 |
| Dihydromyrcenol | 20 |
| Methyl dihydrojasmonate | 150 |
| Indole | 10 |
| Linalyl acetate | 50 |
| Methyl anthranilate | 100 |
| Tobacco odor deodorizing composition of Preparation Ex. 13 | 30 |
| Ethylene brassylate | 10 |
| Hexyl benzoate | 100 |
| Orange oil | 50 |
| Phenylethyl alcohol | 30 |
| o-tert-butylcyclohexyl acetate | 50 |
| Total | 1000 |

(II) The components given in Table 15 below were heated and stirred uniformly at 80 to 85° C., followed by cooling the mixture so as to obtain an oily gel deodorant.

TABLE 15

<Oily gel deodorant>

| Components | Amounts (parts by mass) |
| --- | --- |
| Sodium stearate | 7.5 |
| Purified water | 2.0 |
| Hexylene glycol | 4.0 |

TABLE 15-continued

<Oily gel deodorant>

| Components | Amounts (parts by mass) |
|---|---|
| Dibutyl hydroxy toluene | 0.2 |
| d-limonene | 76.3 |
| Deodorizing composition of Ex. 7 (I) | 10.0 |
| Total | 100.0 |

Example 8

Oily Gel Deodorant

The components given in Table 16 below were heated and stirred uniformly at 80 to 85° C., followed by cooling the mixture so as to obtain an oily gel deodorant.

TABLE 16

<Oily gel deodorant>

| Components | Amounts (parts by mass) |
|---|---|
| Sodium stearate | 7.5 |
| Purified water | 2.0 |
| Hexylene glycol | 4.0 |
| Dibutyl hydroxy toluene | 0.2 |
| d-limonene | 76.3 |
| Tobacco odor deodorizing composition of Preparation Ex. 13 | 10.0 |
| Total | 100.0 |

Example 9

Aerosol Deodorant (I) A deodorizing composition for an aerosol deodorant having the composition shown in Table 17 given below was prepared by using the deodorizing composition prepared in Preparation Example 17.

TABLE 17

<Deodorizing composition for aerosol deodorant>

| Components | Amounts (parts by mass) |
|---|---|
| Benzyl acetate | 50 |
| Benzyl salicylate | 30 |
| Cedryl acetate | 50 |
| Citronellol | 65 |
| Coriandar oil | 30 |
| Lavender oil | 250 |
| Tobacco odor deodorizing composition of Preparation Ex. 17 | 100 |
| Pine needle oil | 150 |
| Rosemary oil | 25 |
| Sage oil | 150 |
| o-tert-butylcyclohexyl acetate | 100 |
| Total | 1000 |

(II) The components (A) shown in Table 18 given below were stirred and dissolved, followed by loading the resultant solution in an aerosol can and subsequently sealing the aerosol can. Then, the component (B) was injected into the aerosol can so as to obtain an aerosol deodorant. A liquefied propane gas, which is generally used in an aerosol deodorant, was used as an aerosol propellant.

TABLE 18

<Aerosol deodorant>

| Components | Amounts (parts by mass) |
|---|---|
| (A) Deodorizing composition of Ex. 9 (I) | 1.0 |
| 95% geraniol denatured alcohol | 48.5 |
| Spherical silica | 0.5 |
| (B) Aerosol propellant (liquefied propane gas) | 50.0 |
| Total | 100.0 |

Example 10

Aerosol Deodorant

The components (A) shown in Table 19 given below were stirred and dissolved, followed by loading the resultant solution in an aerosol can and subsequently sealing the aerosol can. Then, the component (B) was injected into the aerosol can so as to obtain an aerosol deodorant. A liquefied propane gas, which is generally used in an aerosol deodorant, was used as an aerosol propellant.

TABLE 19

<Aerosol deodorant>

| Components | Amounts (parts by mass) |
|---|---|
| (A) Tobacco odor deodorizing composition of Preparation Ex. 17 | 1.0 |
| 95% geraniol denatured alcohol | 48.5 |
| Spherical silica | 0.5 |
| (B) Aerosol propellant (liquefied propane gas) | 50.0 |
| Total | 100.0 |

Example 11

Shampoo

A deodorizing composition for shampoo having the composition shown in Table 20 given below was prepared by using the deodorizing composition prepared in Preparation Example 13.

TABLE 20

<Deodorizing composition for shampoo>

| Components | Amounts (parts by mass) |
|---|---|
| Dodecanal | 4 |
| Benzyl acetate | 40 |
| α-damascon | 10 |
| Eugenol | 30 |
| Garakusolid (trade name; manufactured by IFF Inc.)[1] | 170 |
| Methyl dihydrojasmonate | 100 |
| Heliobouquete (trade name; manufactured by Takasago Koryo Kogyo K.K.)[2] | 80 |

TABLE 20-continued

<Deodorizing composition for shampoo>

| Components | Amounts (parts by mass) |
|---|---|
| Kobanol (trade name, manufactured by Takasago Koryo Kogyo K.K.)[3] | 70 |
| Lemon oil | 150 |
| Levosandole (trade name, manufactured by Takasago Koryo Kogyo K.K.)[4] | 50 |
| p-tert-butyl-α-methylhydrocinnamic aldehyde | 80 |
| Tobacco odor deodorizing composition of Preparation Ex. 13 | 30 |
| Ethylene brassylate | 35 |
| Phenylethyl alcohol | 100 |
| Terpineol | 50 |
| Vanillin | 1 |
| Total | 1000 |

Note:
[1] 1,3,4,6,7,8-hexhydro-4,6,6,7,8,8-hexamehyl-cyclopenta-γ-2-benzopyran
[2] 2-methyl-3-(3,4-methylenedioxyphenyl)-propanal
[3] 4(3)-(4-hydroxy-4-methypentyl)-3-cyclohexene-1-carboxyaldehyde
[4] (E)-(R)-2-ethyl-4-(2,2,3-trimethyl-3-cyclopenten-1-yl)-2-buten-1-ol (II) The components shown in Table 21 given were stirred at 80° C. so as to obtain a suspension, followed by cooling the suspension to 35° C. so as to obtain a shampoo.

TABLE 21

<Shampoo>

| Components | Amounts (parts by mass) |
|---|---|
| Sodium laurylsulfate | 40.00 |
| N-coconut oil fatty acyl-N-carboxy-methoxyethyl-N-carboxymethylethylenediamine disodium | 10.00 |
| Coconut oil fatty acid diethanolamide (2) | 2.00 |
| Butylene glycol | 2.00 |
| Citric acid | 0.35 |
| Sodium chloride | 0.10 |
| Methylparaben | 0.20 |
| Propylparaben | 0.10 |
| Tetrasodium edetoate | 0.10 |
| Purified water | 44.65 |
| Deodorizing composition of Ex. 11 (I) | 0.50 |
| Total | 100.00 |

Example 12

Shampoo

The components shown in Table 22 given were stirred at 80° C. so as to obtain a suspension, followed by cooling the suspension to 35° C. so as to obtain a shampoo.

TABLE 22

<Shampoo>

| Components | Amounts (parts by mass) |
|---|---|
| Sodium laurylsulfate | 40.00 |
| N-coconut oil fatty acyl-N-carboxy-methoxyethyl-N-carboxymethylethylenediamine disodium | 10.00 |
| Coconut oil fatty acid diethanolamide (2) | 2.00 |

TABLE 22-continued

<Shampoo>

| Components | Amounts (parts by mass) |
|---|---|
| Butylene glycol | 2.00 |
| Citric acid | 0.35 |
| Sodium chloride | 0.10 |
| Methylparaben | 0.20 |
| Propylparaben | 0.10 |
| Tetrasodium edetoate | 0.10 |
| Purified water | 44.65 |
| Tobacco odor deodorizing composition of Preparation Ex. 13 | 0.50 |
| Total | 100.00 |

Example 13

Body Shampoo (I) A deodorizing composition for a body shampoo having the composition as shown in Table 23 below was prepared by using the deodorizing composition prepared in Preparation Example 13.

TABLE 23

<Deodorizing composition for body shampoo>

| Components | Amounts (parts by mass) |
|---|---|
| Dodecanal | 50 |
| Karon (Pheizer, trade name)[1] | 5 |
| Chamomile oil | 2 |
| Methyl dihydrojasmonate | 100 |
| Heliobouquet (trade name, manufactured by Takasago Koryo Kogyo K.K.)[2]; | 80 |
| Linalool | 60 |
| Tobacco odor deodorizing composition of Preparation Ex. 13 | 100 |
| Ethylene brassylate | 95 |
| 10-oxahexadecanoride | 50 |
| Isocamphylcyclohexanol | 50 |
| Tetrahydrolinalool | 58 |
| Tonalid (trade name, manufactured by PFW Inc.)[3] | 120 |
| Towanal (trade name, manufactured by Takasago Koryo Kogyo K.K.)[4]; | 10 |
| Tripral (trade name, manufactured by IFF Inc.)[5] | 20 |
| p-tert-butylcyclohexyl acetate | 200 |
| Total | 1000 |

Note:
[1] 7-methyl-3,5-dihydro-2H-benzodioxepin-3-one
[2] 2-methyl-3-(3,4-methylenedioxyphenyl)-propanal
[3] 6-acetyl-1,1,2,4,4,7-hexamethyltetrahydro-naphthalene
[4] 4-(4-methyl-3-pentenyl)-3-cyclohexene-1-carbaldehyde
[5] 2,4-dimethyl-3-cyclohexenylcarboxaldehyde (II) The components given in Table 24 below were stirred at 80° C. so as to obtain a suspension, followed by cooling the suspension to 35° C. so as to obtain a shampoo.

TABLE 24

<Body shampoo>

| Components | Amounts (parts by mass) |
| --- | --- |
| Dibutylhydroxytoluene | 0.05 |
| Methylparaben | 0.10 |
| Propylparaben | 0.10 |
| Tetrasodium edetoate | 0.10 |
| Potassium chloride | 0.20 |
| Glycerin | 5.00 |
| Coconut oil fatty acid diethanolamide(2) | 3.00 |
| Sodium polyoxyethylenelauryl-ether acetate (3E.O.) (30%) | 10.00 |
| Coconut oil fatty acid amide propyl betaine | 25.00 |
| Potassium myristate (40%) | 25.00 |
| Purified water | 30.95 |
| Deodorizing composition of Ex. 13 (I) | 0.50 |
| Total | 100.00 |

Example 14

Body Shampoo

The components given in Table 25 below were stirred at 80° C. so as to obtain a suspension, followed by cooling the suspension to 35° C. so as to obtain a shampoo.

TABLE 25

<Body shampoo>

| Components | Amounts (parts by mass) |
| --- | --- |
| Dibutylhydroxytoluene | 0.05 |
| Methylparaben | 0.10 |
| Propylparaben | 0.10 |
| Tetrasodium edetoate | 0.10 |
| Potassium chloride | 0.20 |
| Glycerin | 5.00 |
| Coconut oil fatty acid diethanolamide(2) | 3.00 |
| Sodium polyoxyethylenelauryl-ether acetate (3E.O.) (30%) | 10.00 |
| Coconut oil fatty acid amide propyl betaine | 25.00 |
| Potassium myristate (40%) | 25.00 |
| Purified water | 30.95 |
| Tobacco odor deodorizing composition of Preparation Ex. 13 | 0.50 |
| Total | 100.00 |

Example 15

Rinse (I) A deodorizing composition for rinse having the composition shown in Table 26 below was prepared by using the deodorizing composition prepared in Preparation Example 13.

TABLE 26

<Deodorizing composition for rinse>

| Components | Amounts (parts by mass) |
| --- | --- |
| Undecanal | 5 |
| Benzyl acetate | 100 |
| Citronellol | 100 |
| Coumarin | 10 |
| Methyl dihydrojasminate | 240 |
| Heliotropin | 80 |
| Iso yee super (trade name, manufactured by IFF Inc.)[1] | 60 |
| Lemon oil | 55 |
| Levosandole (trade name, manufactured by Takasago Koryo Kogyo K.K.)[2] | 30 |
| Tobacco odor deodorizing composition of Preparation Ex. 13 | 30 |
| Ethylene brassylate | 200 |
| Suzaral (trade name, manufactured by Takasago Koryo Kogyo K.K.)[3]; | 10 |
| Vanillin | 10 |
| p-tert-butylcyclohexyl acetate | 80 |
| Total | 1000 |

Note:
[1] 7-acetyl-1,2,3,4,5,6,7,8-octahydro-1,1,6,7-tetramethylnaphthalene
[2] (E)-(R)-2-ethyl-4-(2,2,3-trimethyl-3-cyclopenten-1-yl)-2-buten-1-ol
[3] p-isobutyl-α-methylhydrocinnamic aldehyde (II) A composition having the components shown in Table 27 below was heated uniformly to 80° C. while stirring the composition, followed by cooling the composition to 35° C. so as to obtain a rinse.

TABLE 27

<Rinse>

| Components | Amounts (parts by mass) |
| --- | --- |
| O-[2-hydroxy-3-(trimethylammonio)-propyl]hydroxyethyl cellulose chloride | 0.10 |
| Sodium hydroxide | 0.03 |
| Citric acid | 0.05 |
| Methylparaben | 0.20 |
| Propylparaben | 0.10 |
| Polyoxyethylene cetyl ether (10 E.O.) | 0.50 |
| Cetanol | 1.50 |
| Behenyl alcohol | 3.00 |
| Distearyl dimethyl ammonium chloride (90%) | 0.20 |
| Stearyl trimethyl ammonium chloride (50%) | 1.50 |
| Cetyl 2-ethylhexanoate | 0.50 |
| Methyl polysiloxane | 2.00 |
| Deodorizing composition Example 15 (I) | 0.50 |
| Purified water | 89.82 |
| Total | 100.00 |

Example 16

Rinse

The components shown in Table 28 below were heated and stirred at 80° C. until uniform, followed by cooling the mixture to 35° C. so as to obtain a rinse.

TABLE 28

<Rinse>

| Components | Amounts (parts by mass) |
|---|---|
| O-[2-hydroxy-3-(trimethylammonio)-propyl]hydroxyethyl cellulose chloride | 0.10 |
| Sodium hydroxide | 0.03 |
| Citric acid | 0.05 |
| Methylparaben | 0.20 |
| Propylparaben | 0.10 |
| Polyoxyethylene cetyl ether (10 E.O.) | 0.50 |
| Cetanol | 1.50 |
| Behenyl alcohol | 3.00 |
| Distearyl dimethyl ammonium chloride (90%) | 0.20 |
| Stearyl trimethyl ammonium chloride (50%) | 1.50 |
| Cetyl 2-ethylhexanoate | 0.50 |
| Methyl polysiloxane | 2.00 |
| Tobacco odor deodorizing composition of Preparation Ex. 13 | 0.50 |
| Purified water | 89.82 |
| Total | 100.00 |

Example 17

Yogurt Candy (I) A yogurt flavor of the composition shown in Table 29 below was prepared by using the deodorizing composition prepared in Preparation Example 13.

TABLE 29

<Yogurt flavor>

| Components | Amounts (parts by mass) |
|---|---|
| Ethylvanillin | 2.0 |
| Vanillin | 4.0 |
| Lemon oil | 15.0 |
| Orange oil | 38.0 |
| Lemon terpene-less oil | 1.0 |
| Tobacco odor deodorizing composition of Preparation Ex. 13 | 2.0 |
| Milk base (manufactured by Takasago Koryo Kogyo K.K.) | 20.0 |
| Ester base (manufactured by Takasago Koryo Kogyo K.K.) | 16.0 |
| Acid base (manufactured by Takasago Koryo Kogyo K.K.) | 2.0 |
| Total | 100.0 |

(II) A yogurt candy having the composition shown in Table 30 below was manufactured by using the yogurt flavor prepared in Example 17 (I).

TABLE 30

<Yogurt candy>

| Components | Amounts (parts by mass) |
|---|---|
| Granulated sugar | 540.0 |
| Thick malt syrup | 480.0 |
| Purified water | 160.0 |
| Vegetable hardened oil | 20.0 |
| Lecithin | 0.2 |
| All fat condensed milk | 50.0 |

TABLE 30-continued

<Yogurt candy>

| Components | Amounts (parts by mass) |
|---|---|
| Fermented milk paste | 25.0 |
| Yogurt flavor of Example 17 (I) | 1.0 |

Example 18

Mouth Washing Agent

A mouth wash flavor of the composition shown in Table 31 below was prepared by using the deodorizing composition prepared in Preparation Example 13.

TABLE 31

<Mouth wash flavor>

| Components | Amounts (parts by mass) |
|---|---|
| 1-menthol | 50.0 |
| Peppermint oil top cut | 20.0 |
| Eucalyptus oil | 10.0 |
| Tobacco odor deodorizing composition of Preparation Ex. 13 | 10.0 |
| Anethole | 6.0 |
| Sage oil | 2.0 |
| Eugenol | 1.0 |
| Fennel oil | 0.8 |
| Thyme oil | 0.2 |
| Total | 100.0 |

(II) A mouth washing agent having the composition shown in Table 32 below was prepared by using the mouth wash flavor prepared in Example 18 (I).

TABLE 32

<Mouth washing agent>

| Components | Amounts (parts by mass) |
|---|---|
| 95% ethyl alcohol | 15.00 |
| 70% sorbitol solution | 10.00 |
| Polyoxyethylene hardened castor oil (E O 60) | 2.00 |
| Mouth wash flavor of Example 18 (I) | 0.10 |
| Sodium benzoate | 0.05 |
| Saccharin sodium | 0.02 |
| Purified water | 72.83 |
| Total | 100.00 |

Example 19

Dentifrice (I) A tooth paste flavor having the composition shown in Table 33 below was prepared by using the deodorizing composition prepared in Preparation Example 13.

TABLE 33

<Tooth paste flavor>

| Components | Amounts (parts by mass) |
|---|---|
| Peppermint oil | 35.0 |
| 1-methol | 25.0 |
| Spearmint oil | 10.0 |
| Tobacco odor deodorizing composition of Preparation Ex. 13 | 10.0 |
| Anethole | 8.0 |
| Sweet orange oil | 5.0 |
| Clove oil | 5.0 |
| Lemon oil | 2.0 |
| Total | 100.0 |

(II) A dentifrice having the composition shown in Table 34 below was manufactured by using the tooth paste flavor prepared in Example 19 (I).

TABLE 34

<Dentifrice>

| Components | Amounts (parts by mass) |
|---|---|
| Calcium hydrogen phosphate (Calcium secondary phosphate) | 50.00 |
| Glycerin | 25.00 |
| Sodium carboxymethylcellulose | 1.50 |
| Sodium laurylsulfate | 1.40 |
| Tooth paste flavor of Example 19 (I) | 1.00 |
| Saccharin sodium | 0.20 |
| Sodium benzoate | 0.05 |
| Purified water | 20.85 |
| Total | 100.00 |

Example 20

Stomatic Agent (I) An oral fresh flavor having the composition shown in Table 35 given below was prepared by using the deodorizing composition prepared in Preparation Example 13.

TABLE 35

<Oral fresh flavor>

| Components | Amounts (parts by mass) |
|---|---|
| 1-menthol | 50.0 |
| Lemon oil cold press | 15.0 |
| Peppermint oil | 10.0 |
| 1,8-cineol | 5.0 |
| Lemon oil | 5.0 |
| Tobacco odor deodorizing composition of Preparation Ex. 13 | 5.0 |
| Ethyl alcohol | 10.0 |
| Total | 100.0 |

(II) A stomatic agent having the composition shown in Table 36 below was manufactured by using the oral fresh flavor prepared in Example 20 (I).

TABLE 36

<Stomatic agent>

| Components | Amounts (parts by mass) |
|---|---|
| 95% ethyl alcohol | 50.0 |
| Glycerin | 10.0 |
| Polyoxyethylene hardened castor oil (EO 60) | 2.0 |
| Oral fresh flavor of Example 20 (I) | 1.5 |
| Saccharin sodium | 0.2 |
| Purified water | 36.3 |
| Total | 100.0 |

Example 21

Chewing Gum (I) A flavor for a chewing gum having the composition shown in Table 37 given below was prepared by using the deodorizing composition prepared in Preparation Example 13.

TABLE 37

<Flavor for chewing gum>

| Components | Amounts (parts by mass) |
|---|---|
| Tobacco odor deodorizing composition of Preparation Ex. 13 | 5.0 |
| Peppermint oil | 44.5 |
| Spearmint oil | 10.0 |
| 1-menthol | 5.0 |
| Methyl salicylate | 5.0 |
| Eucalyptus oil | 10.0 |
| Clove oil | 0.5 |
| Total | 100.0 |

(II) A chewing gum having the composition shown in Table 38 below was manufactured by using the flavor for a chewing gum prepared in Example 21 (I).

TABLE 38

<Chewing gum>

| Components | Amounts (parts by mass) |
|---|---|
| Gum base | 20 |
| Powdery sugar | 66 |
| Thick malt syrup | 13 |
| Flavor for chewing gum of Example 21 (I) | 1 |
| Total | 100 |

Example 22

Tablet Candy (I) A flavor for a tablet candy having the composition shown in Table 39 below was prepared by using the deodorizing composition prepared in Preparation Example 13.

TABLE 39

<Flavor for table candy>

| Components | Amounts (parts by mass) |
| --- | --- |
| Tobacco odor deodorizing composition of Preparation Ex. 13 | 1 |
| l-menthol | 17 |
| Peppermint oil | 1 |
| Eucalyptus oil | 1 |
| Gum Arabic | 80 |
| Total | 100 |

(II) A tablet candy having the composition shown in Table 40 below was manufactured by using the flavor for a tablet candy prepared of Example 22 (I).

TABLE 40

<Tablet candy>

| Components | Amounts (parts by mass) |
| --- | --- |
| Sugar | 98 |
| Lubricant, emulsifying agent | 1 |
| Flavor for tablet candy of Example 22 (I) | 1 |
| Total | 100 |

Example 23

Flavor for Gelatin Capsule (I) A flavor for a gelatin capsule having the composition shown in Table 41 below was prepared by using the deodorizing composition prepared in Preparation Example 13.

TABLE 41

<Flavor for gelatin capsule>

| Components | Amounts (parts by mass) |
| --- | --- |
| Peppermint oil | 55 |
| Tobacco odor deodorizing composition of Preparation Ex. 13 | 5 |
| Middle chain fatty acid triglyceride (MCT) | 40 |
| Total | 100 |

(II) A gelatin capsule base material having the composition shown in Table 42 below was prepared by using the flavor for a gelatin capsule prepared in Example 23 (I).

TABLE 42

<Gelatin capsule base material>

| Components | Amounts (parts by mass) |
| --- | --- |
| Gelatin | 5.0 |
| Purified water | 94.9 |
| Flavor for gelatin capsule of Ex. 23 (I) | 0.1 |
| Total | 100.0 |

The deodorizing effect in respect of the tobacco sidestream smoke and the usability were evaluated for each of the granular deodorants (Examples 1 and 2), the mist deodorants (Examples 3 and 4), the water-based gel deodorants (Examples 5 and 6), the oily gel deodorants (Examples 7 and 8), the aerosol deodorants (Examples 9 and 10), the shampoos (Examples 11 and 12), the body shampoos (Examples 13 and 14), the rinses prepared (Examples 15 and 16), the yogurt candies (Example 17), the mouth washing agent (Example 18), the dentifrice (Example 19), the stomatic agent (Example 20), the chewing gum (Example 21), the tablet candy (Example 22), and the gelatin capsule base material (Example 23). The deodorizing effect and the usability were found to be satisfactory in all of these Examples. Examples 24-41 and Comparative Examples 1-6

Each of the formulated perfumes (sidestream smoke odor reducing agent) shown in Table 43 below was added by the ordinary perfume-imparting technology to tobacco shreds in the amount shown in Table 43, and the tobacco shreds were wrapped with the same wrapper paper sheet so as to prepare a predetermined number of cigarettes for each of the formulated perfumes. Also, a predetermined number of reference cigarettes were prepared in exactly the same procedure, except that the formulated perfume was not added.

The sidestream smoke odor was evaluated by the room method described above. The results are shown also in Table 43.

TABLE 43

| | Perfume | | Results of Evaluation | | | |
| --- | --- | --- | --- | --- | --- | --- |
| Cigarettes | Perfume | Amount added per cig. (μg) | Intensity of Overall Odor | Improvement of Odor | Intensity of Tobacco Odor | Number of Panelists |
| Comp. Ex. 1 | OCT | 31 | 0.48 | 0.59 | 0.48 | 29 |
| Comp. Ex. 2 | LIN | 81 | 0.50 | 0.70 | 0.30 | 30 |
| Comp. Ex. 3 | CAR | 15 | 0.47 | 0.60 | 0.50 | 30 |
| Comp. Ex. 4 | MAN | 16 | 0.52 | 0.63 | 0.44 | 27 |
| Comp. Ex. 5 | SIN | 10 | 0.49 | 0.68 | 0.29 | 31 |
| Comp. Ex. 6 | OEO | 10 | 0.49 | 0.68 | 0.29 | 31 |
| Example 24 | Comp. of Prep. Ex. 1 | 112 | 0.53 | 0.64 | 0.40 | 30 |

TABLE 43-continued

| Cigarettes | Perfume | Perfume Amount added per cig. (μg) | Results of Evaluation | | | |
|---|---|---|---|---|---|---|
| | | | Intensity of Overall Odor | Improvement of Odor | Intensity of Tobacco Odor | Number of Panelists |
| Example 25 | Comp. of Prep. Ex. 2 | 46 | 0.53 | 0.58 | 0.44 | 30 |
| Example 26 | Comp. of Prep. Ex. 3 | 47 | 0.50 | 0.61 | 0.46 | 28 |
| Example 27 | Comp. of Prep. Ex. 4 | 41 | 0.45 | 0.67 | 0.50 | 29 |
| Example 28 | Comp. of Prep. Ex. 5 | 96 | 0.40 | 0.71 | 0.41 | 27 |
| Example 29 | Comp. of Prep. Ex. 6 | 97 | 0.47 | 0.65 | 0.33 | 30 |
| Example 30 | Comp. of Prep. Ex. 7 | 97 | 0.44 | 0.70 | 0.28 | 27 |
| Example 31 | Comp. of Prep. Ex. 8 | 31 | 0.48 | 0.65 | 0.60 | 27 |
| Example 32 | Comp. of Prep. Ex. 9 | 25 | 0.48 | 0.67 | 0.38 | 29 |
| Example 33 | Comp. of Prep. Ex. 10 | 26 | 0.44 | 0.61 | 0.33 | 33 |
| Example 34 | Comp. of Prep. Ex. 11 | 41 | 0.50 | 0.60 | 0.27 | 30 |
| Example 35 | Comp. of Prep. Ex. 12 | 72 | 0.48 | 0.71 | 0.26 | 31 |
| Example 36 | Comp. of Prep. Ex. 13 | 153 | 0.46 | 0.75 | 0.21 | 28 |
| Example 37 | Comp. of Prep. Ex. 14 | 350 | 0.39 | 0.79 | 0.21 | 33 |
| Example 38 | Comp. of Prep. Ex. 15 | 800 | 0.45 | 0.79 | 0.17 | 29 |
| Example 39 | Comp. of Prep. Ex. 16 | 400 | 0.50 | 0.70 | 0.30 | 30 |
| Example 40 | Comp. of Prep. Ex. 17 | 800 | 0.45 | 0.69 | 0.24 | 29 |
| Example 41 | Comp. of Prep. Ex. 18 | 153 | 0.33 | 0.73 | 0.20 | 30 |

<Explanation of symbols in the Table>
OCT: n-octanal;
LIN: linalool;
CAR: l-carvone;
MAN: methyl anthranilate;
SIN: sinensal;
OEO: orange peel essential oil sinensal fraction As apparent from the results of evaluation given in Table 43, the cigarettes carrying the sidestream smoke odor reducing agent of the present invention permit improving the odor and lowering the intensity of the tobacco odor without substantially increasing the intensity of the overall odor, compared with the cigarette of the Comparative Example.

Examples 42 to 48

The formulated perfume (sidestream smoke odor reducing agent) prepared in Preparation Example 18 was applied to the applied portions shown in Table 44 given below, not to the tobacco shreds, in the amounts shown in Table 44 so as to obtain a prescribed number of cigarettes. An ethylene-vinyl acetate copolymer was used as the seam paste. The application of the formulated perfume to the wrapper paper sheet was conducted by directly spraying the formulated perfume to the wrapper paper sheet.

Also, a prescribed number of reference cigarettes were prepared in exactly the same procedure, except that the formulated perfume was not added.

The sidestream smoke odor was evaluated by the room method described previously in respect of each of the cigarettes thus prepared. Table 44 also shows the result.

TABLE 44

| Cigarettes Ex. No. | Sidestream smoke reducing agent | | Results of Evaluation | | | |
|---|---|---|---|---|---|---|
| | Added Portion | Amount added* (μg) | Intensity of Overall Odor | Improvement of Odor | Intensity of Tobacco Odor | Number of Panelists |
| Example 42 | Seam paste | 50 | 0.46 | 0.58 | 0.31 | 30 |
| Example 43 | | 100 | 0.42 | 0.66 | 0.34 | 30 |
| Example 44 | | 170 | 0.47 | 0.75 | 0.28 | 30 |

TABLE 44-continued

| Cigarettes Ex. No. | Sidestream smoke reducing agent | | Results of Evaluation | | | |
|---|---|---|---|---|---|---|
| | Added Portion | Amount added* (μg) | Intensity of Overall Odor | Improvement of Odor | Intensity of Tobacco Odor | Number of Panelists |
| Example 45 | Wrapper | 25 | 0.37 | 0.59 | 0.41 | 30 |
| Example 46 | paper | 35 | 0.37 | 0.63 | 0.40 | 30 |
| Example 47 | | 40 | 0.27 | 0.73 | 0.27 | 30 |
| Example 48 | | 70 | 0.39 | 0.80 | 0.15 | 30 |

Note)
*Amount added per cigarette

As apparent from the experimental data given in Table 44, the sidestream smoke odor reducing agent of the present invention permits producing the desired effect by the addition of the agent to not only the threaded tobacco leaves but also to the seam paste or the wrapper paper sheet.

Example 49

Concerning the cigarette obtained in Example 41, the functional evaluation in respect of the items shown in Table 45 given below was performed by the odor bag method (cigarette) described previously by five expert panelists who have received the expert training for the tobacco odor. Table 45 also shows the results. The results shown in Table 45 represent the average value of the results of evaluation by the five panelists.

TABLE 45

| Evaluating items | Results of Evaluations Amount* of sidestream smoke odor reducing agent added (μg) | | | |
|---|---|---|---|---|
| | Not added | 85 | 170 | 340 |
| Overall odor | 3.2 | 2.2 | 2.1 | 2.0 |
| Tobacco odor | 2.8 | 2.6 | 1.8 | 1.7 |
| Refreshment | 0.4 | 0.8 | 1.8 | 1.3 |
| Scorching odor | 3.0 | 2.4 | 1.8 | 1.9 |
| Stimulating odor | 2.2 | 1.6 | 1.5 | 1.4 |
| Smoky odor | 3.4 | 2.8 | 2.2 | 1.8 |
| Balance | 0.8 | 1.3 | 1.8 | 2.0 |

Note)
*Amount added per cigarette

As apparent from the experimental data given in Table 45, the cigarette of the present invention permits not only lowering the overall odor and the tobacco odor but also improving the refreshment and lowering the scorching odor, the stimulating odor and the smoky odor, compared with the reference cigarette.

What is claimed is:

1. A tobacco odor deodorizing composition consisting of at least one component from each of five component groups (I) to (V) given below:
    (I) octanal, nonanal and/or decanal;
    (II) linalool;
    (III) carvone;
    (IV) methyl anthranilate and/or N-methyl anthranilate; and
    (V) sinensal and/or orange peel essential oil sinensal fraction, and
wherein said components are present at a ratio (I):(II):(III):(IV):(V) by mass of 2 to 6:3 to 10:0.5 to 2.5:0.5 to 20:0.1 to 3.

2. The composition according to claim 1, which consists of octanal, linalool, carvone, methyl anthranilate and either sinensal or an orange peel essential oil sinensal fraction.

3. A tobacco odor deodorant consisting of:
    a tobacco odor deodorizing composition, which consists of at least one component from each of five component groups (I) to (V) given below:
    (I) octanal, nonanal and/or decanal;
    (II) linalool;
    (III) carvone;
    (IV) methyl anthranilate and/or N-methyl anthranilate; and
    (V) sinensal and/or orange peel essential oil sinensal fraction; and
    a carrier carrying the deodorizing composition, and
    wherein said components are present at a ratio (I):(II):(III):(IV):(V) by mass of 2 to 6:3 to 10:0.5 to 2.5:0.5 to 20:0.1 to 3.

4. The deodorant according to claim 3, wherein the deodorizing composition consists of octanal, linalool, carvone, methyl anthranilate and either sinensal or an orange peel essential oil sinensal fraction.

5. The deodorant according to claim 3, wherein the deodorant is in a form of a liquid deodorant, a solid deodorant, a powdery deodorant, a gel deodorant, a mist deodorant, or an aerosol deodorant.

6. Perfumes, foods, an external remedy for the skin, an oral composition, or a sanitary material, which contains 0.0005 to 20 mass % of the tobacco odor deodorant of claim 3.

7. A cigarette consisting of a tobacco rod including a tobacco filler material and a cigarette wrapper paper sheet wrapping an outer circumferential surface of the tobacco filler material, said cigarette carrying a sidestream smoke odor reducing agent consisting of at least one component from each of at least three component groups selected from five component groups (I) to (V) given below:
    (I) octanal, nonanal and/or decanal;
    (II) linalool;
    (III) carvone;
    (IV) methyl anthranilate and/or N-methyl anthranilate; and
    (V) sinensal and/or orange peel essential oil sinensal fraction.

8. The cigarette according to claim 7, wherein a ratio (I):(II):(III):(IV):(V) by mass of the component groups (I), (II), (III), (IV) and (V), when present, is set at 2 to 6:3 to 10:0.5 to 2.5:0.5 to 20:0.1 to 3.

9. The cigarette according to claim 7, wherein the sidestream smoke odor reducing agent consists of octanal, linalool, carvone, methyl anthranilate and either sinensal or an orange peel essential oil sinensal fraction.

10. The cigarette according to claim 7, which carries the sidestream smoke odor reducing agent such that at least 0.01 mg in total of the components are contained in each cigarette.

11. The cigarette according to claim 7, which carries the sidestream smoke odor reducing agent at the tobacco filler material.

12. The cigarette according to claim 7, which carries the sidestream smoke odor reducing agent on the cigarette wrapper paper sheet.

13. The cigarette according to claim 7, which carries the sidestream smoke odor reducing agent at the seam paste.

14. A tobacco package housing tobacco rods each including a tobacco filler material and a cigarette wrapper paper sheet wrapping an outer circumferential surface of the tobacco filler material, said tobacco package containing a sidestream smoke odor reducing agent consisting of at least three component groups selected from five component groups (I) to (V) given below:
(I) octanal, nonanal and/or decanal;
(II) linalool;
(III) carvone;
(IV) methyl anthranilate and/or N-methyl anthranilate; and
(V) sinensal and/or orange peel essential oil sinensal fraction.

15. The tobacco odor deodorant according to claim 3, wherein the tobacco odor deodorizing composition consist of octanal, linalool, carvone, methyl anthranilate and either sinensal or an orange peel essential oil sinensal fraction.

16. The cigarette according to claim 7, wherein the sidestream smoke odor reducing agent consist of at least one component from each of the five component groups (I) to (V) at a ratio (I):(II):(III):(IV):(V) by mass of 2 to 6:3 to 10:0.5 to 2.5:0.5 to 20:0.1 to 3.

17. The cigarette according to claim 16, wherein the sidestream smoke odor reducing agent consists of octanal, linalool, carvone, methyl anthranilate and either sinensal or an orange peel essential oil sinensal fraction.

18. A cigarette consisting of:
a tobacco rod including a tobacco filler material and a cigarette wrapper paper sheet wrapping an outer circumferential surface of the tobacco filler material; and
a filter plug provided at one end of the tobacco rod, said cigarette carrying a sidestream smoke odor reducing agent consisting of at least one component from each of at least three component groups selected from five component groups (I) to (V) given below:
(I) octanal, nonanal and/or decanal;
(II) linalool;
(III) carvone;
(IV) methyl anthranilate and/or N-methyl anthranilate; and
(V) sinensal and/or orange peel essential oil sinensal fraction.

19. The cigarette according to claim 18, wherein the sidestream smoke odor reducing agent consists of at least one component from each of the five component groups (I) to (V) at a ratio (I):(II):(III):(IV):(V) by mass of 2 to 6:3 to 10:0.5 to 2.5:0.5 to 20:0.1 to 3.

20. The cigarette according to claim 18, wherein the sidestream smoke odor reducing agent consists of octanal, linalool, carvone, methyl anthranilate and either sinensal or an orange peel essential oil sinensal fraction.

21. The cigarette according to claim 18, which carries the sidestream smoke odor reducing agent on the cigarette wrapper paper.

22. A cigarette consisting of:
a tobacco rod including a tobacco filler material and a cigarette wrapper paper sheet wrapping an outer circumferential surface of the tobacco filler material;
a seam paste bonding the cigarette wrapper; and
optionally, a filter plug provided at one end of the tobacco rod,
and wherein said cigarette carrying a sidestream smoke odor reducing agent consists of at least one component from each of at least three component groups selected from five component groups (I) to (V) given below:
(I) octanal, nonanal and/or decanal;
(II) linalool;
(III) carvone;
(IV) methyl anthranilate and/or N-methyl anthranilate; and
(V) sinensal and/or orange peel essential oil sinensal fraction, wherein the sidestream smoke odor reducing agent is added to the seam paste.

23. The cigarette according to claim 22, wherein a ratio (I):(II):(III):(IV):(V) by mass of the component groups (I), (II), (III), (IV), and (V) is set at 2 to 6:3 to 10:0.5 to 2.5:0.5 to 20:0.1 to 3.

24. The cigarette according to claim 22, wherein the sidestream smoke odor reducing agent consists of at least one component from each of the five component groups (I) to (V) a ratio (I):(II):(III):(IV):(V) by mass of 2 to 6:3 to 10:0.5 to 2.5:0.5 to 20:0.1 to 3.

25. The cigarette according to claim 22, wherein the sidestream smoke odor reducing agent consists of octanal, linalool, carvone, methyl anthranilate and either sinensal or an orange peel essential oil sinensal fraction.

* * * * *